United States Patent [19]

DeLuca et al.

[11] Patent Number: 5,086,191

[45] Date of Patent: Feb. 4, 1992

[54] INTERMEDIATES FOR THE SYNTHESIS OF 19-NOR VITAMIN D COMPOUNDS

[75] Inventors: Hector F. DeLuca, Deerfield; Heinrich K. Schnoes; Kato L. Perlman, both of Madison, all of Wis.

[73] Assignee: Wisconsin Alumni Research Foundation, Madison, Wis.

[21] Appl. No.: 705,932

[22] Filed: May 28, 1991

[51] Int. Cl.⁵ ............................................... C07C 3/00
[52] U.S. Cl. .................................................... 552/653
[58] Field of Search ........................................ 552/653

[56] References Cited

PUBLICATIONS

Perlman, et al., *Tetrahedron Letters*, vol. 31 (13) pp. 1823-1824, 1990.

*Primary Examiner*—Howard T. Mars
*Assistant Examiner*—Kimberly J. Kestler
*Attorney, Agent, or Firm*—Andrus, Sceales, Starke & Sawall

[57] ABSTRACT

New intermediate compounds that can be used effectively for the synthesis of a broad range of 1α-hydroxy-19-nor-vitamin D compounds. These novel intermediates are characterized by a group selected from hydroxy methyl (—CH$_2$OH), carboxaldehyde (—CHO), and carboxy ester (—COOAlkyl) at the carbon 22 position of the side chain of a 19-nor-vitamin D nucleus. Intermediates of this type are useful for the introduction of side chain units and thus represent important synthons for the preparation of many different 19-nor-vitamin D compounds.

1 Claim, No Drawings

INTERMEDIATES FOR THE SYNTHESIS OF 19-NOR VITAMIN D COMPOUNDS

BACKGROUND OF THE INVENTION

The hormone, 1a, 25-dihydroxyvitamin $D_3$, is known to be a highly potent regulator of calcium homeostasis in animals, and more recently its activity in cellular differentiation has been established, v. Ostrem, Y. Tanaka, J. Prahl, H. F. DeLuca and N. Ikekawa, *Proc. Natl. Acad. Sci, USA,* (1987), 84, 2610. Many structural analogs have been prepared and tested and some of these have been found to exhibit an interesting separation of activities in cell differentiation and calcium regulation. This difference in activity may be useful in the treatment of some cancers and osteoporosis, H. Sai, S Takatsuto, N. Ikekawa, I. Tanaka and H. F. DeLuca, *Chem. Pharm. Bull,* (1986), 34, 4508.

Recently, a new class of vitamin D analogs has been discovered, the so-called 19-nor-vitamin D compounds, which as shown by the general structure below, are characterized by the replacement of the ring A-exocyclic methylene group (carbon 19), typical of the vitamin D system, by two hydrogen atoms.

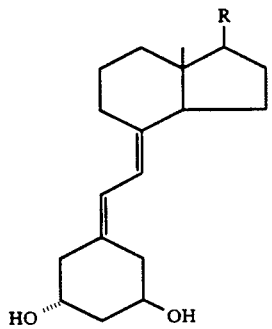

The group R in the above structure represents a steroid side chain as it occurs in any of the natural vitamin D compounds, or in synthetic analogs thereof. A specific example of a 19-nor-vitamin D compound is 1α,25-dihydroxy-19-nor-vitamin $D_3$. Biological testing of such 19-nor-analogs revealed an activity profile characterized by high potency in inducing differentiation of malignant cells, with very low calcium mobilizing activity. Thus, such compounds are potentially useful as therapeutic agents for the treatment of malignancies.

A method of synthesis of 19-nor-vitamin D compounds has been reported by Perlman et al., *Tetrahedron Letters* 13, 1823 (1990). However, this method, which involves the removal of the C-19-methylene group in an existing vitamin D compound is not well suited for the larger scale preparation of 19-nor analogs.

DISCLOSURE OF THE INVENTION

This invention provides new intermediates that can be used effectively for the synthesis of a broad range of 1α-hydroxy-19-nor-vitamin D compounds. These novel intermediates are characterized by the general structure I.

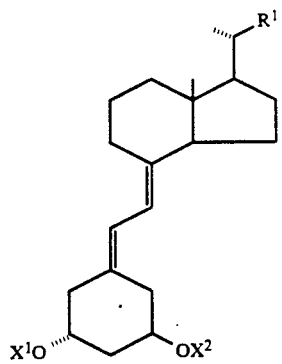

where $X^1$ and $X^2$, which may be the same or different, represent hydrogen or hydroxy-protecting groups, and where $R^1$ is selected from the group consisting of hydroxy methyl (—$CH_2OH$), carboxaldehyde (—CHO), and carboxy ester (—COOAlkyl). Intermediates of this type are useful for the introduction of side chain units and thus represent important synthons for the preparation of many different 19-nor-vitamin D compounds.

As used in the description, and in the claims, the term "hydroxy-protecting group" refers to any group commonly used for the protection of hydroxy functions during subsequent reactions, including, for example, acyl or alkylsilyl groups such as trimethylsilyl, triethylsilyl, t-butyldimethylsilyl and analogous alkyl or arylsilyl radicals, or alkoxyalkyl groups such as methoxymethyl, ethoxymethyl, methoxyethoxymethyl, tetrahydrofuranyl or tetrahydropyranyl. A "protected-hydroxy" is a hydroxy function derivatized by one of the above hydroxy-protecting groupings. "Alkyl" represents a straight-chain or branched hydrocarbon radical or 1 to 10 carbons in all its isomeric forms, such as methyl, ethyl, propyl, isopropyl, butyl, isobutyl, pentyl, etc., and the terms "hydroxyalkyl," "fluoroalkyl" and "deuteroalkyl" refer to such an alkyl radical substituted by one or more hydroxy, fluoro or deuterium groups, respectively. An "acyl" group is an alkanoyl group of 1 to 6 carbons in all its isomeric forms, or an aroyl group, such as benzoyl, or halo-, nitro-, or alkyl-substituted benzoyl groups, or an alkoxycarbonyl group of the type Alkyl—O—CO—, such as methoxycarbonyl, ethoxycarbonyl, propyloxycarbonyl, etc., or a dicarboxylic acyl group such as oxalyl, malonyl, succinoyl, glutaroyl, or adiopoyl. The term "aryl" signifies a phenyl-, or an -alkyl-, nitro-, or halo-substituted phenyl group. The term alkoxy signifies the group, alkyl—O—.

A method for the preparation of compounds of structure I above is disclosed herein. This method comprises the condensation of a bicyclic ketone having the structure II,

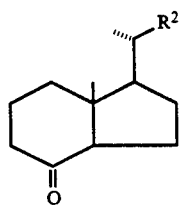

where $R^2$ is a hydroxy-protected hydroxymethyl group, a protected carboxaldehyde group, such as the carboxaldehyde diethyl- or ethylene acetal, or carboxyalkyl group, with a phosphine oxide derivative, of the formula

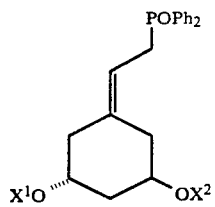

where $X^1$ and $X^2$ represent hydroxy-protecting groups.

Required bicyclic ketone starting materials are known, or can be prepared by known methods [(see, for example, Baggiolini et al., *J. Org. Chem.* 51, 3098 (1986); Sardina et al., *J. Org. Chem.* 51, 1264 (1986); Kocienski et al., *J. Chem. Soc. Perkin Trans.* 1. 834 (1978)].

The required phosphine oxide unit is prepared as outlined in Scheme I and further described in specific Example 1.

As shown in Scheme I, the starting material for the preparation of the ring-A unit is the commercially available (1R,3R,4R,5R) (-)quinic acid, designated as compound 1 in Scheme I herein, which already contains the correct stereochemistry of the 1- and 3-hydroxy groups for the desired 19-nor-vitamin D compound. Esterification with methanol in the presence of a catalytic amount of acid (e.g. p-toluene sulfonic acid), followed by treatment with tert-butyldimethylsilyl chloride and triethylamine in dimethyl formamide gave the protected methyl ester 2. It should be noted that esterification with higher alkanols (e.g. ethanol, propanol, etc.) under analogous conditions produces the corresponding higher esters, and that similarly other hydroxy-protecting groups (e.g. other alkyl or arylsilyl groups, or alkoxyalkyl groups) can be introduced at this stage by known methods. Such alternative esters or hydroxy-protected derivatives of 2 can likewise be used in subsequent conversions according to Scheme I. Reduction of the ester with diisobutylaluminum hydride gave triol 3, and subsequent sodium periodate oxidation produced the cyclohexanone derivative 4. The 4-hydroxy group was protected with an alkylsilyl group to give 5. A Peterson reaction with ethyl (trimethylsily)acetate in the presence of base in anhydrous tetrahydrofuran gave the unsaturated ester 6. Other alkyl (trimethylsilyl) acetate esters (e.g. where alkyl=methyl, propyl, butyl, etc.) can be used in this reaction to give alkyl esters analogous to 6 (e.g. the corresponding methyl, propyl, butyl esters, etc.). Partial deprotection of the 4-trimethylsilyloxy group with dilute acetic acid in tetrahydrofuran gave 7. The deoxygenation of the 4-hydroxy group was accomplished by a free radical fragmentation procedure [D. H. R. Barton and S. W. McCombie, *J. Chem. Soc. Perkin Trans.* 1, 1574 (1975); D. H. R. Barton and W. B. Motherwell, *Pure & Appl. Chem.*, 53, 15 (1981)]. Thus, ester 7 was converted to the corresponding thioimidazolide 8 by treatment with 1,1-thioicarbonyl-diimidazole in an organic solvent, and subsequent radical deoxygenation with tributyltin hydride in the presence of a radical initiator (AIBN) gave the protected cyclohexylidene ester 9. The latter was reduced to the allylic alcohol 10 with diisobutylaluminum hydride which was then converted to the allylic chloride 11 by reaction with the complex made from N-chlorosuccinimide and dimethyl sulfide [(E. J. Corey, C. U. Kim, M. Takeda, *Tetrahedron Letters*, 4339 (1972)] and finally transformed to the desired phosphine oxide 12 on treatment with lithium diphenylphosphide followed by oxidation with hydrogen peroxide.

A specific embodiment of the condensation reaction between a bicyclic ketone and phosphine oxide 12 is shown in Scheme II, and is further described in Example 2. As shown in Scheme II, the reaction comprises the treatment of the phosphine oxide 12 with a strong base so as to generate the carbanion, which then reacts with the bicyclic ketone 13 to produce the desired 19-nor-intermediate (14).

By oxidation of the primary alcohol group in compound 14, according to known conditions [Kutner et al., *J. Oro. Chem.* 53, 3450 (1988)], there is obtained the corresponding 22-aldehyde intermediate, i.e. compound I, where $R^1$ is a carboxaldehyde (—CHO) group. Alternatively, this compound can also be produced by a condensation, under the above conditions, between the phosphine oxide 12, and bicyclic ketone II, where $R^2$ is a protected carboxaldehyde function. Subsequent removal of the aldehyde-protecting group under conventional conditions provides the 19-nor-compound I where $R^1$ is CHO. Likewise, the corresponding 19-nor-vitamin D 22-ester (e.g. compound I, where $R^1$ is COOMe) is prepared by an entirely analogous condensation reaction between phosphine oxide 12 and the bicyclic ketone II, where $R^2$ is —COOMe. In any of the above products, the hydroxy-protecting groups ($X^1$ and $X^2$) can be removed under conventional conditions to produce the corresponding 1,3-hydroxy compounds if desired.

The above described 22-hydroxymethyl, 22-carboxaldehyde, or 22-carboxyester products can be used as intermediates for the introduction of a broad range of side chains, according to the methods of, for example, DeLuca et al., U.S. Pat. No. 4,847,012; Andrews et al., *J. Org. Chem.* 51, 4819 (1986); Kutner et al., *J. Org. Chem.* 53, 3450 (1988), to provide the desired 1α-hydroxy-19-nor-vitamin D compounds in many different side chain modifications. Illustrative of such uses are the Grignard coupling of hydroxy-protected 3-hydroxy-3-methylbutylmagnesium bromide with the tosylate derivative of compound 14 ($X^3$=SO₂PhMe) to obtain hydroxy-protected 1α,25-dihydroxy-19-nor vitamin $D_3$, or the coupling of 2,3-dimethylbutyl phenylsulphone with the corresponding 22-aldehyde derivative 14 to obtain, after desulfonylation, 1α-hydroxy-19-nor-vitamin $D_2$ in hydroxy-protected form.

The invention is further described by the following specific examples. In these examples, Arabic numerals (e.g. 1, 2, 3, . . . ), designating specific synthetic products, refer to the structures so numbered in Schemes I and II.

EXAMPLE 1

(a) (1R,3R,4R,5R) Methyl 1 3 5-Bis (tert-butyldimethylsilyloxy)-1.4-Dihydroxycyclohexane-Carboxylate(2)

p-Toluene sulfonic acid (0.5 g) was added to a solution of quinic acid 1 (12.74 g, 66.3 mmol) in methanol. The solution was stirred for 24 h. Solid $NaHCO_3$ (1.0 g) was added and after 15 min. the solution was filtered and concentrated to give 12.61 g (62.16 mmol) of the methyl ester in 92% yield.

tert-Butyldimethylsilyl chloride (6.73 g, 44.62 mmol) was added to a solution of methyl (1R,3R,4R,5R)(-) quinicate 1 (3.68 g, 17.85 mmol) and triethyl amine (6.2 mL, 44.62 mmol) in 44 mL of anhydrous dimethyl formamide at 0° C. with stirring. After 4 h the solution was warmed to room temperature and stirring continued for another 14 h. The solution was poured into water and extracted with ether. The combined organic layers were extracted with brine, dried over anhydrous MgSO$_4$, filtered and concentrated. The residue was purified by column chromatography on silica gel, eluting with 5-10% ethyl acetate in hexane mixtures, to give 4.6 g (60%) of 2 as a white solid. M.p. 82°-82.5° C. (after recrystallization from hexanes). 1H NMR (CDCl3, 500 MHz) δ4.53 (bs, 1 H), 4.36 (bs, 1H), 4.11 (ddd, 1 H), 3.76 (s, 3H), 3.42 (dd, 1H), 2.31 (bs, 1H), 2.18 (bd, 1 H), 2.05 (ddd, 2H), 1.82 (dd, 1 H), 0.91 (s, 9 H), 0.89 (s, 9 H) 0.15 (s, 3 H), 0.14 (s, 3 H), 0.11 (s, 3 H), 0.09 (s, 3 H) MS m/e (relative intensity) 377 (70), 227 (91).

(b) (1R,3R,4R,5R) 3.5-Bis (tert,-butyldimethylsilyloxy)-1,4-dihydroxy]-1-hydroxymethylcyclohexane (3).

Diisobutyl aluminum hydride (45 mL, 45.0 mmol, 1.0 M in hexanes) was added to a solution of the ester 2 (3.26 g, 7.5 mmol) in ether (45 mL) at −78° C. After 20 min. the solution was warmed to −23° C. and stirred for 2 h. The solution was diluted with ether and then 2 N potassium sodium tartrate was slowly added. The solution was warmed to room temperature and stirred for 15 min. The ether layer was separated and the aqueous layer extracted with ether. The combined ether layers were extracted with brine, dried over anh. MgSO$_4$, filtered and concentrated. The material was further purified by column chromatography on silica gel with 25% ethyl acetate/hexanes to give 83% of 3 (2.52 g, 6.20 mmol), Mp. 108°-109° C. from hexanes. 1H NMR (CDCl3, 500 MHz) δ4.52 (bs, 1 H), 4.12 (ddd, 1 H) 3.40 (dd, 1 H) (dd, 2 H), 2.28 (d, 1 H) 2.11 (dd, 1 H) 2.00 (ddd, 2 H), 1.52 (dd, 1 H), 1.33 (dd, 1 H) 0.91 (s, 9, H) 2.00 (ddd, 2 H), 1.52 (dd, 1 H), 1.33 (dd, 1 H), 0.91 (s, 3 H), 0.11 (s, 3 H). MS m/e (relative intensity) : 349 (8), 331 (13), 239 (12), 199 (100).

(c) (3R,4R,5R) [3.5-Bis (tert.-butyldimethylsilyloxy)-4-hydroxyl]-1-cyclohexanone (4).

Sodium periodate saturated water (28.5 mL) was added to the triol 3 (1.9 g, 4.7 mol) in methanol (124 mL) at 0° C. The solution was stirred for 1 h, then poured into water and extracted with ether. The combined ether fractions were washed with brine, dried over anhydrous MgSO$_4$, filtered and concentrated to give 1.72 g (4.59 mmol) of 4 (98%). No further purification was required. Mp. 98°-100° C. from hexanes. 1H NMR (CDCl3, 500 MHz) δ4.28 (m, 2 H), 3.80 (bs, 1 H), 2.77 (dd, 1 H, J=14.3, 3.4 Hz), 2.59 (dd, 1H, J=13.1, 10.7 Hz), 2.45 (dd, 1 H, J=14.1, 5.2 Hz) 2.25 (bd, 1 H, J=15.9 Hz), 0.90 (s, 9 H), 0.85 (s, 9 H), 0.08 (s, 34 H), 0.08 (s, 3 H), 0.06, (s, 6 H). MS m/e (relative intensity) 317 (62), 231 (16), 185 (76), 143 (100).

(d) (3R,4R,5R) [3.5-Bis(tert.-butydimethylsilyloxy)-4-trimethylsiloxy]-1-cyclohexanone (5)

N-(Trimethylsilyl)imidazole (2.52 mL, 26.67 mmol) was added to a solution of the ketoalcohol (4) (1.56 g, 4.167 mmol) in methylene chloride (38 mL). The solution was stirred for 20 h. Water (1 mL) was added and the solution stirred for 30 min. Brine and methylene chloride was added. The brine was extracted with methylene chloride. The combined methylene chloride fractions were dried with anh. MgSO$_4$, filtered and concentrated. The residue was further purified by column chromatography on silica gel with 10% ethyl acetate in hexane to give 5 (1.76 g, 3.95 mmol) in 95% yield. 1H NMR (CDCl3, 500 mHz) δ4.25 (m, 1 H), 4.13 (m, 1, H), 4.04 (m, 1 H), 2.74 (ddd, 2 H), 2.38 (dd, 1 H), 2.19 (dd, 1 H), 0.90 (s, 9 H), 0.86 (s, 9 H), 0.16 (s, 9 H), 0.07 (bs, 12 H). MS m/e (relative intensity): 431 (5), 389 (100), 299 (45), 257 (28).

(e) (3R,4R,5R) Ethyl [3,5-bis(tert-butyldimethylsiyloxy)-4-hydroxy]-cyclohexylidene carboxylate. (7).

n.Butyl lithium (1.83 mL, 3.106 mmol) 1.5 M in hexanes was added to a solution of diisopropylamine (0.43 mL, 3.106 mmol) in anhydrous tetrahydrofuran (2.10 mL) under argon at −78° C. with stirring. After 15 min. the solution was warmed to 0° C. for 15 min. and then cooled to −78° C. and ethyl (trimethylsilyl) acetate (0.57 mL, 3.11 mmol) was added. After 15 min. the protected keto compound 5 (0.6934 g, 1.55 mmol) in anhydrous tetrahydrofuran (2.1+1.0 mL) was added. The solution was stirred for 2 h at −78° C. Water and additional ether were added. The water was extracted with ether and the combined ether fractions were extracted with brine, dried over anhydrous MgSO4, filtered and evaporated. The residue (the protected ester 6) was dissolved in tetrahydrofuran (5 mL); acetic acid (5 mL), and water (1 mL) were added. The solution was stirred for 72 h, then diluted with ether. Saturated sodium bicarbonate was slowly added until no more carbon dioxide evolution was evident. The ether was separated and the bicarbonate solution extracted with ether. The combined ether fractions were extracted with brine, dried over anhydrous MgSO$_4$, filtered and concentrated. The product was further purified by column chromatography, and eluted with ethyl acetate-hexane mixtures (10% to 25% ethylacetate in hexane) to give in 86% yield (two steps) 7. (0.544 g, 1.135 mmol) MS m/e (relative intensity) 429 (4), 399 (6), 387 (100), 341 (46).

(f) (3R,4R,5R) Ethyl [3.5-Bis(tert.-butyldimethylsilyloxy)-4-imidazolyl-thiocarbonyloxy-] cyclohexylidenecarboxylate (8)

1,1-thiocarbonyldiimidazole (0.131 g, 0.735 mmol) was added to a solution of the hydroxy ester (7) (0.163 g, 0.37 mmol) in methylene chloride (1.64 mL). The solution was stirred for 60 h. Silica gel was added and the solution concentrated. The residue was added to a column of silica gel and the material eluted with 25% ethyl acetate in hexane to obtain 8 in 87% yield (0.178 g, 0.32 mmol).

(g) (3R,5R) Ethyl [3.5-Bis-(tert.-butyldimethylsilyloxy)]-cyclohexylidene carboxylate (9)

Tributyltin hydride (0.72 mL, 2.66 mmol) was added to a solution of AIBN (17 mg), and the thionoimidazole 8 (0.59 g, 1.06 mmol) in degased toluene (106 mL). The solution was heated with stirring to 100° C. for 2 h and then concentrated. The residue was further purified by column chromatography on silica gel eluting with hexane, following with 3% and 25% ethyl acetate in hexane to obtain 0.322 g (0.75 mmol) 9 in 71% yield.

1H NMR (CDCl3, 500 MHz) δ5.70 (s, 1 H), 4.13 (m, 4 H), 3.05 (dd, J=6.74, 6.16 Hz 1 H), 2.78 (dd, J=6.96, 2.75 Hz, 1 H), 2.38 (dd, J=6.51, 3.25 Hz, 1 H) 2.15 (dd,

J=7.74, 6.48 Hz, 1 H) 1.80 (m, 1 H), 1.70 (m, 1 H), 1.26 (t, J=7.29 Hz, 3 H), 0.87 (s, 9 H), 0.85 (s, 9 H), 0.04 (s, 12 H). MS m/e (relative intensity) : 413 (14), 371 (100), 213 (23).

(h) (3R,5R) [3,5-Bis(tert.-butyldimethylsilyloxy)cyclohexylidene]ethanol (10)

A solution of 96 mg ester 9 (0.22 mmol) in 2 mL of anhydrous toluene was treated at −78° C. under argon with 0.62 mL (0.92 mmol) of a 1.5 M solution of diisobutylaluminum hydride in toluene. After the addition, stirring was continued for 1 h at −78° C. The reaction mixture was then quenched by the addition of 2N potassium sodium tartrate, the organic phase was separated, and the aqueous phase extracted with ethyl acetate. The combined organic phases were washed with water and brine and dried over anhydrous MgSO₄, filtered and evaporated. The residue was purified by fast filtration through a silica gel column, using hexane, followed by hexane-ethyl acetate (10:1) as eluent, to give 58 mg (68%) alcohol 10 as a white solid.

$^1$H NMR (500 MHz) δ0.06 (br s, 12 H), 0.87 (s, 18 H), 1.80 (m, 1 H), 2.05 (dd, 1 H), 2.18 (br dd J=13, 11 Hz, 1 H), 2.34 (m, 1 H), 4.02 (m, 2 H), 4.13 (m, 2 H), 5.60 (br t, J=7.08 1 H). MS m/e (relative intensity) 237 (85), 211 (83), 171 (100).

(i) (3R,5R) [3.5-Bis(tert.-butyldimethylsilyloxy)cyclohexylidene]1-chloroethane (11)

A solution of 50mg (0 37 mmol) N-chlorosuccinimide in 2 mL of anhydrous dichloromethane was treated at 0° C. under argon with 30 μL (0.41 mmol) dimethyl sulfide. A white precipitate formed. The mixture was stirred an additional 15 min. at 0° C., then cooled to −25° C. and treated with 50 mg (0.13 mmol) of the alcohol 10 dissolved in 0.5 mL of anhydrous dichloromethane. The mixture was stirred under argon for 30 min. at −20° C. and then at 0° C. for 30 min. The reaction mixture was poured on ice, and extracted with ethyl acetate. The organic phase was washed with brine, dried over anhydrous MgSO₄ filtered and evaporated. The residue was purified by fast filtration through a silica gel column, eluting with 5% ethyl acetate in hexane to give 52 mg (quant) of the chloro compound 11. $^1$H NMR (CDCl₃, 500 MHz), δ0.06 (s, 12 H), 0.89 (s, 18 H), 1.73 (br dd, 1 H), 2.22 (m, 1 H) 2.30 (m, 1 H), 2.32 (m, 1 H), 4.04 (dd, J=7.3, 10.8 Hz, 2 H), 4.11 (dd, J=2.87, 10.46 Hz, 2 H), 5.51 (brt 1 H). MS m/e (relative intensity) : 237 (93), 215 (52), 189 (79), 105 (100).

(j) (3R,5R)-[Bis(tert.-butyldimethylyloxy)-cyclohexylidenelethyl-diphenylphosphine oxide (12).

40 μL (60 μmol) n.Butyl lithium (1.5 M in hexanes) was added to 10 μL (60 μmol) diphenylphosphine in 30 μL anhydrous tetrahydrofuran at 0° C. with stirring under argon. The orange solution was treated at 0° C. with 20 mg (50 μmol) of the allylic chloride 11 in 300+200 μL anhydrous tetrahydrofuran. The resulting yellow solution was stirred an additional 40 min at 0° C. and quenched by the addition of water. Solvents were evaporated under reduced pressure and the residue was dissolved in chloroform. The chloroform layer was shaken twice with 5% hydrogen peroxide. The chloroform layer was separated and washed with aqueous sodium sulfite, water and brine, dried over anhydrous MgSO₄, filtered and evaporated. The residue was dissolved in 20% 2-propanol in hexane and passed through a silica SepPak and purified by HPLC (Zorbax-Sil 9.4×25 cm column, 20% 2-propanol in hexane) to give 5.5 mg (22%) of the phosphine oxide 12.

UV (EtOH):λ$_{max}$258,265,272 nm, $^1$H NMR (CDCl₃, 500 MHz) δ0.01 (ms, 12 H), 0.85 (m s, 18 H) 1.65 (m, 2 H), 1.91 (m, 1 H) 2.00 (m, 1 H), 2.22 (br d J=3.2 Hz 1 H), 3.05 (dt, J=8.5, 14.9 Hz, 1 H) 3.14 (dt, J=8.5, 14.9 Hz, 1 H), 3.98 (br s 1 H), 5.28 (q, 1 H), 7.46 (m, Ar-5 H), 7.73 (m, Ar-5 H). MS m/e (relative intensity) : 570 (M+, 1) 513 (100), 381 (46), 306 (20), 202 (55), 75 (20).

EXAMPLE 2

1α, 22-Dihydroxy-19-nor-vitamin D compound 14.

20 mg (35 μmol) phosphine oxide 12 was dissolved in 500 μL anhydrous tetrahydrofuran, cooled to 0° C. and 35 μL (50 μmol) n.butyl lithium (1.5 molar in hexanes) added under argon with stirring. The mixture was cooled to −78° C. and 5 mg (20 μmol) protected ketone 13 (X³=Ac) was added in 200 μL+100 μL anhydrous tetrahydrofuran. The mixture was stirred under argon at −78° C. for 2 h and then at 0° C. for 16 h. 20% ethyl acetate in hexane was added and the organic phase washed with saturated ammonium chloride solution, 10% NaHCO₃ solution, brine, dried over anhydrous MgSO₄, filtered and evaporated. The residue was dissolved in 10% ethyl acetate in hexane, passed through a silica SepPak and purified by HPLC in 10% ethyl acetate in hexane (Zorbax Sil 9.4×25 cm column) to give the protected 19-nor vitamin compound 14 (X³=Ac). $^1$H NMR (CDCl₃, 500 MHz) δ0.10 and 0.90 (large singlets, t-butyl-H), 0.56 (3 H, s, 18-CH₃), 1.25 (3H, d, J=7 Hz, 21-CH₃), 2.06 (3H, s, COCH₃), 3.80 and 4.09 (2H, m, 22-H₂), 4.11 (1H, m, 3α-H), 4.22 (1H, m, 1β-H), 5.83 (1H, d, J=11 Hz, 7-H), 6.16 (1H, d, J=11 Hz, 6-H). The 22-acetoxy function is cleaved by treatment with lithium aluminum hydride under conventional conditions to obtain compound 14, where X³ represents H.

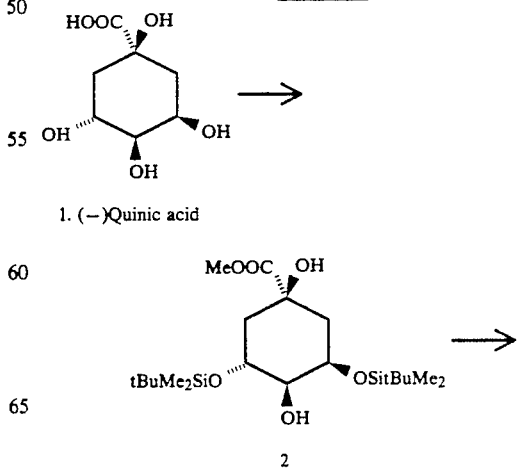

Scheme I 5,086,191
-continued
Scheme I
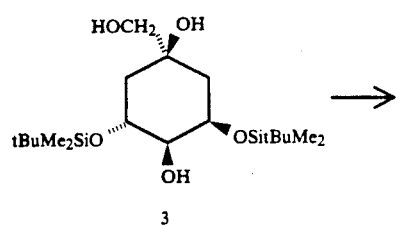
3
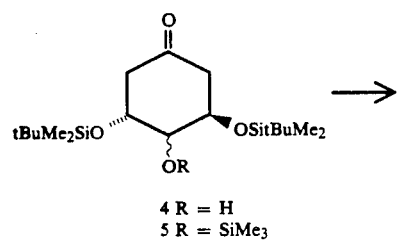
4 R = H
5 R = SiMe₃
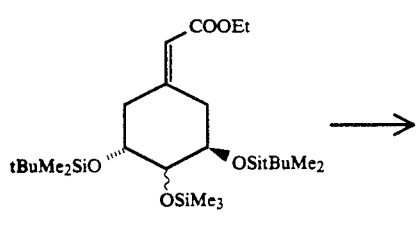
6
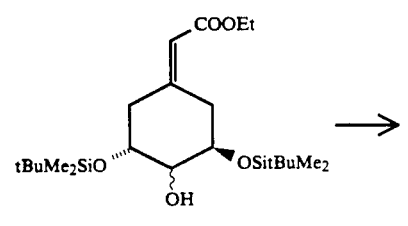
7
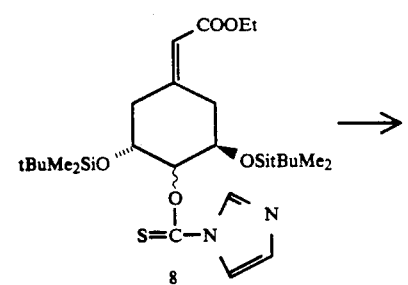
8
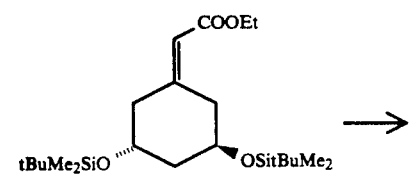
9
-continued
Scheme I
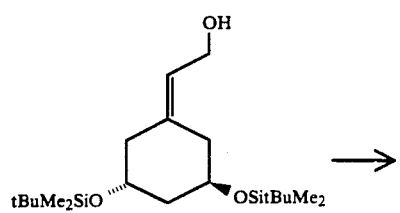
10
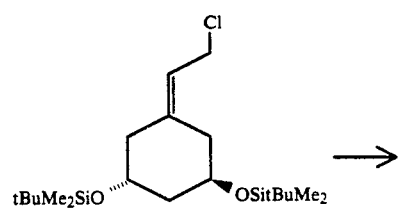
11
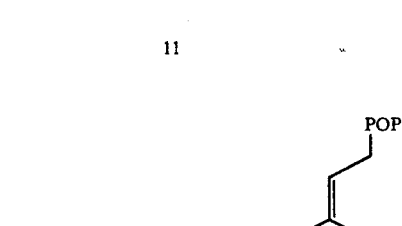
12
Scheme II
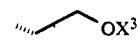
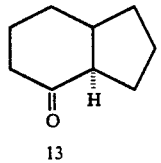 + 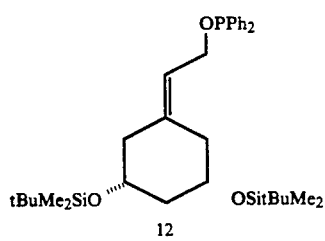 $\xrightarrow{\text{n.BuLi, THF}}$
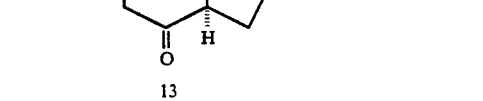

-continued
Scheme II
We claim:
1. A compound of the formula
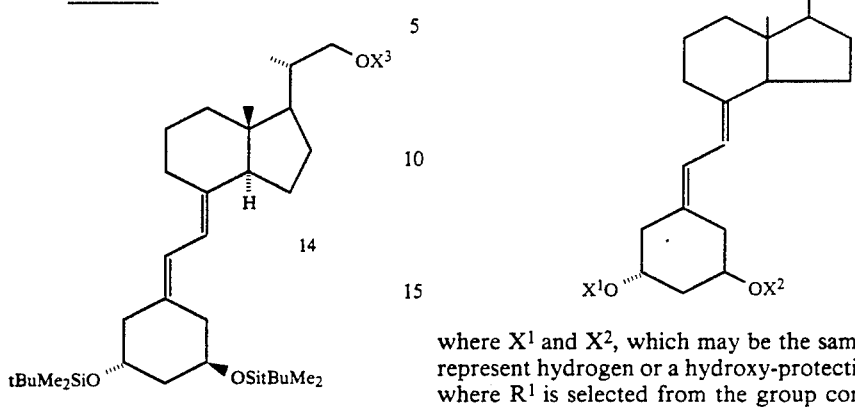
where $X^1$ and $X^2$, which may be the same or different, represent hydrogen or a hydroxy-protecting group, and where $R^1$ is selected from the group consisting of hydroxy-methyl, hydroxy-protected hydroxymethyl, carboxaldehyde (—CHO), and carboxyalkyl (—COOAlkyl).
* * * * *

UNITED STATES PATENT AND TRADEMARK OFFICE
CERTIFICATE OF CORRECTION

PATENT NO. : 5,086,191
DATED : May 28, 1991
INVENTOR(S) : HECTOR F. DeLUCA ET AL

It is certified that error appears in the above-identified patent and that said Letters Patent is hereby corrected as shown below:

In Column 1, Line 4, between the title and the "Background of the Invention" section insert the following:

--- This invention was made with United States Government support awarded by the National Institute of Health (NIH), Grant #DK-14881. The United States Government has certain rights in this invention. ---

Signed and Sealed this

Twenty-eighth Day of September, 1993

Attest:

BRUCE LEHMAN

Attesting Officer

Commissioner of Patents and Trademarks